US009820786B2

(12) United States Patent
Vaidya (10) Patent No.: US 9,820,786 B2
(45) Date of Patent: *Nov. 21, 2017

(54) KNEE HINGE FIXATION APPARATUS AND METHOD FOR APPLICATION THEREOF

(71) Applicant: Rahul Vaidya, Tecumseh (CA)

(72) Inventor: Rahul Vaidya, Tecumseh (CA)

(*) Notice: Subject to any disclaimer, the term of this patent is extended or adjusted under 35 U.S.C. 154(b) by 301 days.

This patent is subject to a terminal disclaimer.

(21) Appl. No.: 14/168,001

(22) Filed: Jan. 30, 2014

(65) Prior Publication Data

US 2015/0209092 A1 Jul. 30, 2015

(51) Int. Cl.
*A61B 17/80* (2006.01)
*A61F 2/38* (2006.01)
*A61B 17/56* (2006.01)

(52) U.S. Cl.
CPC .............. *A61B 17/80* (2013.01); *A61B 17/56* (2013.01); *A61F 2/384* (2013.01); *A61B 2017/567* (2013.01)

(58) Field of Classification Search
CPC ......... A61B 17/58; A61B 17/60; A61B 17/64; A61B 17/6416; A61B 17/6425; A61B 17/6433; A61B 17/68; A61B 17/80; A61B 17/8033; A61B 17/8038; A61B 17/8042; A61B 17/8047; A61B 17/8052; A61B 17/8057; A61B 17/8061; A61B 2017/567
See application file for complete search history.

(56) References Cited

U.S. PATENT DOCUMENTS

| 4,637,382 A * | 1/1987 | Walker | A61B 17/6425 606/55 |
| 5,827,286 A * | 10/1998 | Incavo | A61B 17/8009 606/282 |
| 6,364,909 B1 * | 4/2002 | McGee | A61L 31/026 623/16.11 |
| 2002/0156474 A1 * | 10/2002 | Wack | A61B 17/1728 606/281 |
| 2004/0102776 A1 * | 5/2004 | Huebner | A61B 17/1728 606/281 |
| 2004/0116930 A1 * | 6/2004 | O'Driscoll | A61B 17/8061 606/281 |
| 2006/0116679 A1 * | 6/2006 | Lutz | A61B 17/02 606/86 B |
| 2007/0173843 A1 * | 7/2007 | Matityahu | A61B 17/80 606/916 |
| 2008/0161861 A1 * | 7/2008 | Huebner | A61B 17/8033 606/286 |
| 2008/0275552 A1 * | 11/2008 | Makower | A61B 17/68 623/13.13 |
| 2008/0275555 A1 * | 11/2008 | Makower | A61B 17/68 623/14.12 |
| 2008/0275558 A1 * | 11/2008 | Clifford | A61B 17/68 623/20.14 |

(Continued)

*Primary Examiner* — Eric S Gibson
(74) *Attorney, Agent, or Firm* — David W. Schumaker (57) ABSTRACT

An orthopaedic implant knee hinge and surgical method for minimally invasive insertion of the orthopaedic implant knee hinge. The apparatus and method stabilizes the knee in patients after ligament surgery, conventional fixation of supracondylar and intracondylar fractures of the femur and/or tibial plateau and proximal tibia fractures. The knee hinge is inserted subcutaneously (but supra-muscularly) on one of both of the medial or lateral side of the knee.

10 Claims, 10 Drawing Sheets

(56) References Cited

U.S. PATENT DOCUMENTS

| | | | |
|---|---|---|---|
| 2008/0275562 A1* | 11/2008 | Clifford | A61B 17/68 623/20.21 |
| 2008/0275563 A1* | 11/2008 | Makower | A61B 17/68 623/20.21 |
| 2008/0275564 A1* | 11/2008 | Makower | A61B 17/68 623/20.21 |
| 2008/0300637 A1* | 12/2008 | Austin | A61B 17/74 606/290 |
| 2009/0014016 A1* | 1/2009 | Clifford | A61B 17/88 128/898 |
| 2009/0234462 A1* | 9/2009 | Mullaney | A61B 17/8061 623/47 |
| 2009/0318976 A1* | 12/2009 | Gabriel | A61F 2/3836 606/283 |
| 2010/0030277 A1* | 2/2010 | Haidukewych | A61B 17/8061 606/286 |
| 2010/0137996 A1* | 6/2010 | Clifford | A61B 17/68 623/23.41 |
| 2010/0318086 A1* | 12/2010 | Winemaker | A61B 17/683 606/70 |
| 2011/0034924 A1* | 2/2011 | Tan | A61B 17/6425 606/59 |
| 2011/0112639 A1* | 5/2011 | Regala | A61B 17/56 623/13.12 |
| 2011/0130794 A1* | 6/2011 | Vaidya | A61B 17/80 606/281 |
| 2011/0264216 A1* | 10/2011 | Makower | A61B 17/68 623/13.12 |
| 2012/0010665 A1* | 1/2012 | Vaidya | A61B 17/80 606/281 |
| 2013/0013067 A1* | 1/2013 | Landry | A61B 17/56 623/14.12 |
| 2013/0138218 A1* | 5/2013 | Landry | A61F 2/38 623/20.14 |
| 2013/0304208 A1* | 11/2013 | Clifford | A61F 2/38 623/13.12 |
| 2014/0194907 A1* | 7/2014 | Bonutti | A61B 17/8866 606/151 |
| 2014/0257292 A1* | 9/2014 | Embleton | A61B 17/8061 606/71 |
| 2014/0257501 A1* | 9/2014 | Lowe | A61B 17/1764 623/20.22 |
| 2015/0005831 A1* | 1/2015 | Sands | A61B 17/8061 606/298 |
| 2015/0112343 A1* | 4/2015 | Medoff | A61B 17/1725 606/64 |
| 2015/0173812 A1* | 6/2015 | Masson | A61B 17/80 606/70 |
| 2015/0209092 A1* | 7/2015 | Vaidya | A61F 2/384 606/71 |
| 2015/0282848 A1* | 10/2015 | Vaidya | A61B 17/8057 606/291 |
| 2015/0289910 A1* | 10/2015 | Mirghasemi | A61B 17/8014 606/71 |

* cited by examiner

KNEE HINGE FIXATION APPARATUS AND METHOD FOR APPLICATION THEREOF

FIELD OF THE INVENTION

The present invention relates generally to orthopedic implants and minimally invasive methods for insertion thereof. Specifically the present invention relates to an orthopaedic implant knee hinge and surgical method for minimally invasive insertion thereof.

BACKGROUND OF THE INVENTION

FIG. 1 depicts an anteromedial aspect of knee. The knee joint joins the thigh with the lower leg and consists of two articulations: one between the femur 1 and tibia 2, and one between the femur 1 and patella 3. It is the largest joint in the human body and is very complicated. The knee is a pivotal hinge joint, which permits flexion and extension as well as a slight medial and lateral rotation. Since in humans the knee supports nearly the whole weight of the body, it is vulnerable to acute injury.

Figure 1A:
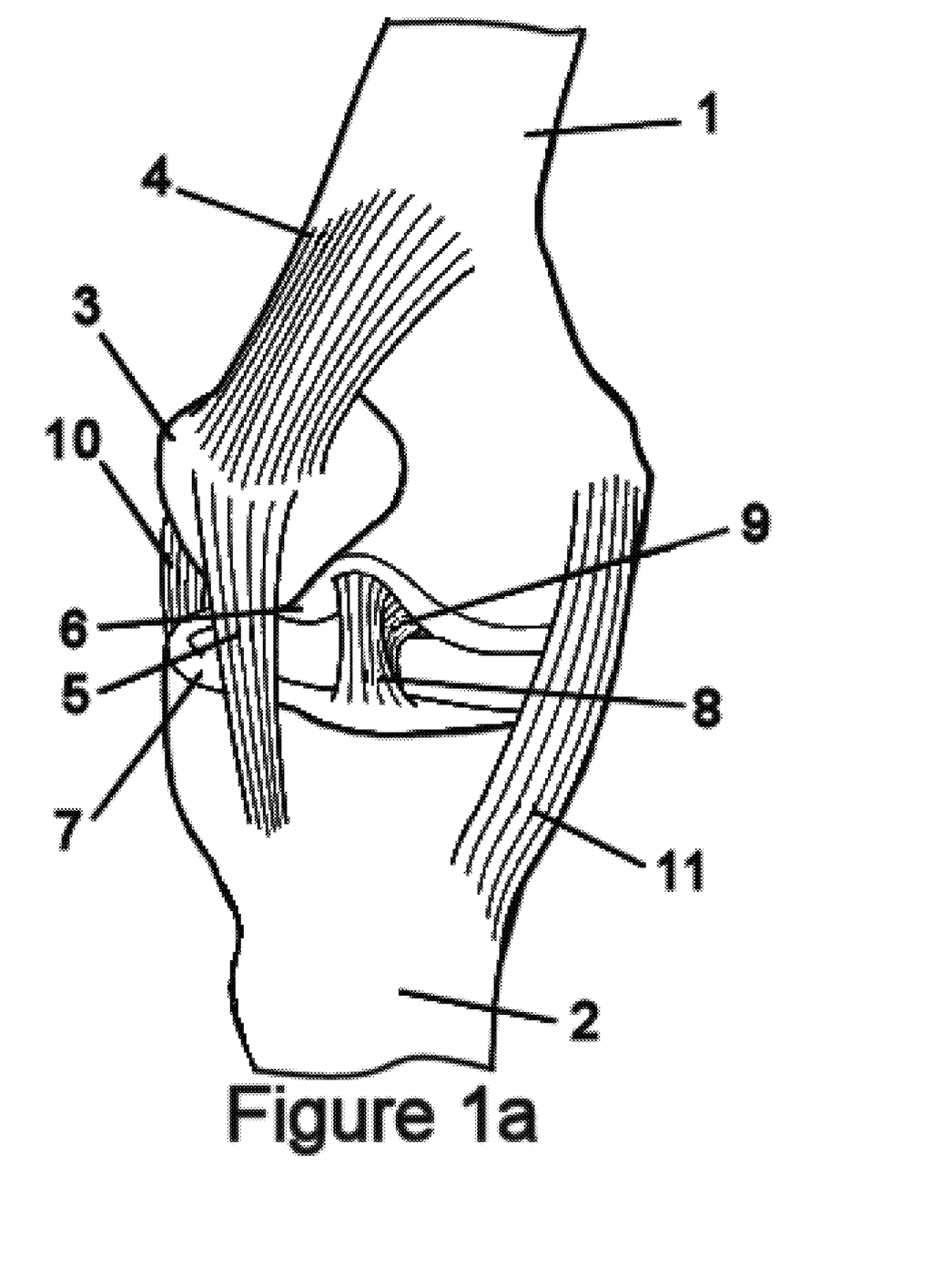
FIG. 1a depicts an anteromedial aspect of knee.

The quadriceps tendon 4 connects the femur 1 to the patella 3 and the patellar tendon 5 connects the patella 3 to the tibia 2. The articular cartilage 6 ensures supple knee movement while the meniscus 7 serves to protect the ends of the bones from rubbing on each other and to effectively deepen the tibial sockets into which the femur 1 attaches.

The ligaments surrounding the knee joint offer stability by limiting movements and, together with several menisci and bursae, protect the articular capsule. Knee laxity, due to ligament injury, can cause significant instability to the knee joint thereby predisposing the joint to further instability and additional injury. The medial collateral ligament (MCL) 11 and lateral collateral ligament (LCL) 10 provide side to side stability of the knee joint. Injury to the MCL 11 or LCL 10 can result in lateral instability of the knee.

The anterior cruciate ligament (ACL) 8 is responsible for controlling the forward glide of the tibia 2 in relation to the femur 1. This movement is called "anterior tibial translation." The ACL 8, in combination with the other ligaments, of a healthy knee joint restrict the rotation or twisting of the knee. Injury to the ACL 8 can result in rotational and anterior instability of the knee.

The posterior cruciate ligament (PCL) 9 is the primary restraint to post translation of the tibia 2 on the femur 1 and acts as a secondary restraint to varus/valgus movements and external rotation. Injury to the PCL 9 can result in posterior instability of the knee whereby the patient feels that the knee can "pop-out" of place. PCL 9 injuries are the least common form of knee instability injury.

An injury or tear of any one of the aforementioned ligament predisposes the knee joint to secondary injuries to the other ligaments, as well as to the meniscus 7 and articular cartilage 6 of the knee. Approximately 50% of all ACL 8 injuries occur in combination with damage to the meniscus 7, articular cartilage 6 or other ligaments (9, 10, 11). Protecting and supporting a weakened knee joint after injury or pre or post-operatively, from the medial, lateral or rotational forces exerted upon the knee during walking, squatting and other movements is the primary purpose of a knee orthosis device for knee instability. Unfortunately such knee orthoses do not always work, especially with in big or obese patients.

Supracondylar and Intracondylar Fractures of the Femur

Figure 1B:
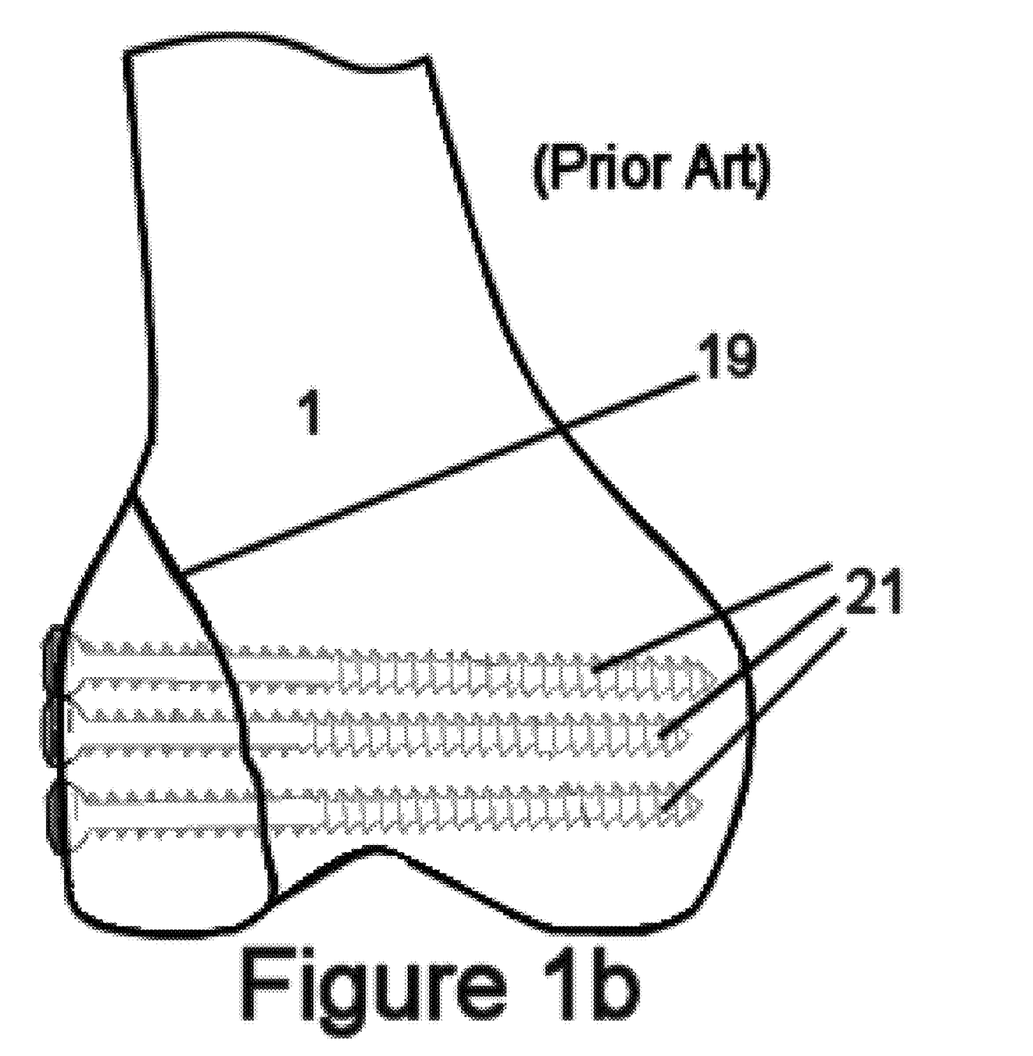
FIG. 1b depicts the conventional fixation of supracondylar and intracondylar fractures of the femur using only bone screws.
Figure 1C:
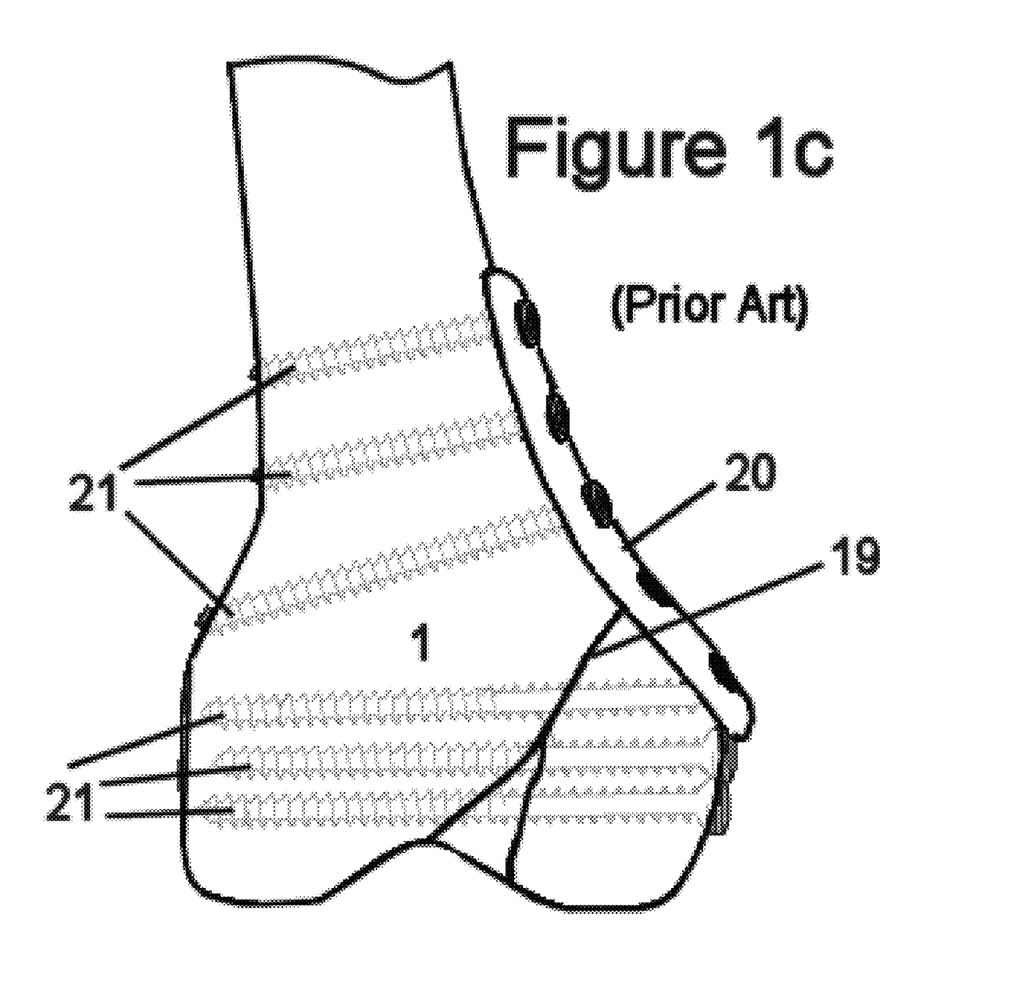
FIG. 1c depicts the conventional fixation of supracondylar and intracondylar fractures of the femur using bone screws and a bone plate.

The rounded ends of the femur are called condyles. There is a type of fracture of the lower end of the femur that starts above the condyles and may pass down into the joint. There is a great deal of variation in the pattern of these fractures. At one extreme is a simple transverse fracture which does not enter the joint. At the other there may be splintering of the bone and multiple fragments including joint surface. The more severe injuries are caused by high energy trauma and may be open fractures. Fractures of the kneecap and tibial plateau may be involved as well. These injuries are amongst the most challenging fractures to treat. FIGS. 1*b* and 1*c* show the conventional means to fix the fractures 19 in the supracondylar and intracondylar regions. Bone screws 21 with or without bone plates 20 are typically used to fix these fractures 19. Unfortunately, with fixation by these conventional techniques, there is generally no ability to bear weight on the leg and the leg may be unable to bend at the knee, causing reduced range of motion in the patient's leg after healing.

Tibial Plateau and Proximal Tibia Fractures

The flat parts of the tibia which form a joint with the femur are called the tibial plateau. On the outside, or lateral side, of the knee is the lateral tibial plateau and on the inside, or medial side, is medial tibial plateau. Compression forces may be too great for this region and the lower end of the femur may be driven into the tibial plateau on the inner or outer side—or occasionally both.

Figure 1D:
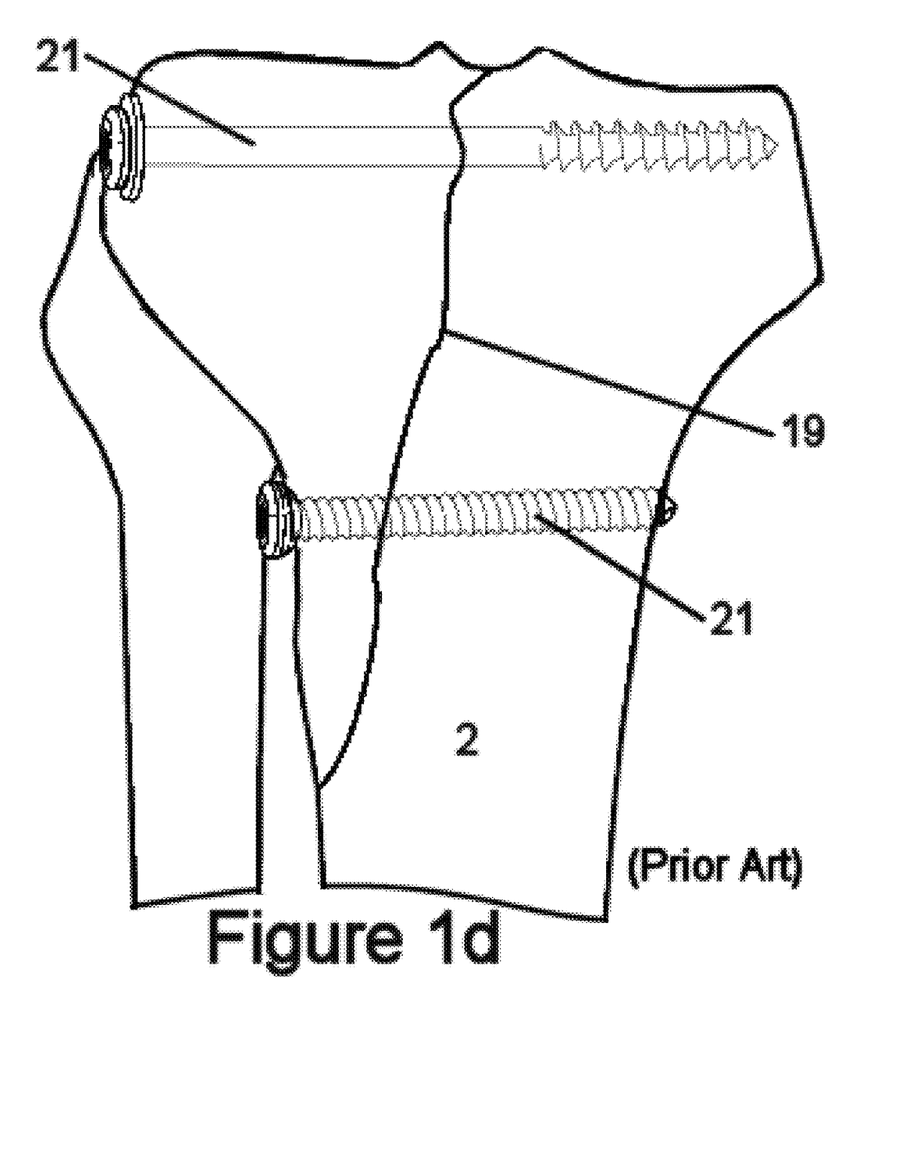
FIG. 1d depicts the conventional fixation of tibial plateau and proximal tibia fractures using only bone screws.
Figure 1E:
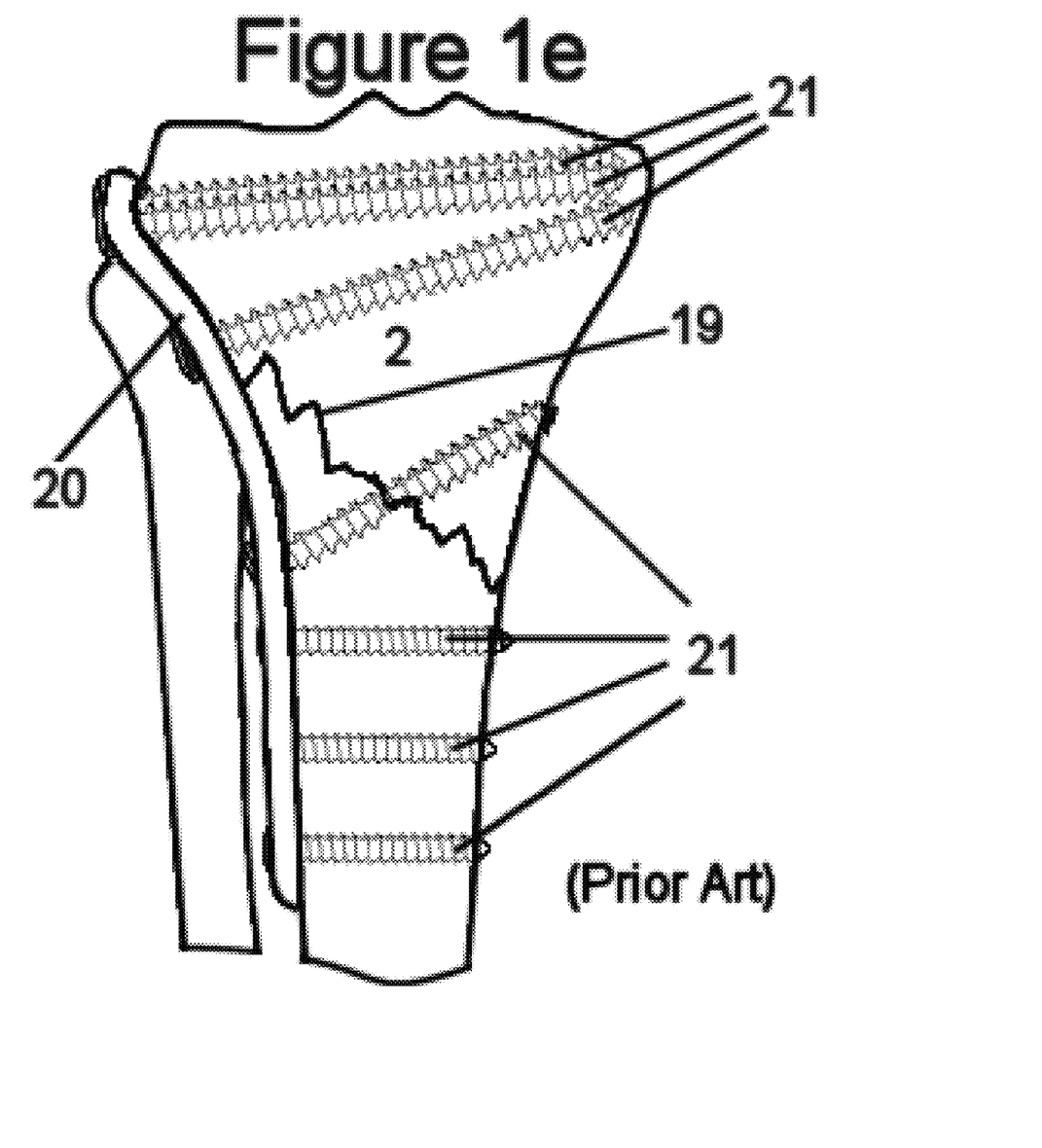
FIG. 1e depicts the conventional fixation of tibial plateau and proximal tibia fractures using bone screws and a bone plate.

These are severe and troublesome injuries which damage the weight bearing surfaces of this major joint. The focus of treatment of a tibial plateau fracture is to restore the smoothness of the joint surface as best as possible. Like supracondylar and intracondylar fractures of the femur there is a wide spectrum of tibial plateau fractures ranging from simple injuries which damage one plateau to extensive fractures with many fragments and involvement of the shaft of the tibia. FIGS. 1*d* and 1*e* show the conventional means to fix the fractures 19 in the tibial plateau and proximal tibia regions. Bone screws 21 with or without bone plates 20 are typically used to fix these fractures 19. Again, with fixation by these conventional techniques, there is generally no ability to bear weight on the leg and the leg may be unable to bend at the knee, causing reduced range of motion in the patient's leg after healing.

Thus, there is a need in the art for an apparatus and method for stabilizing the knee in patients after ligament surgery and after fixation of supracondylar and intracondylar fractures of the femur or tibial plateau and proximal tibia fractures.

SUMMARY OF THE INVENTION

An orthopaedic implant knee hinge and surgical method for minimally invasive insertion thereof in the subcutaneous fat layer between the skin and the muscle. That is, the implant is placed subcutaneously, but supra-muscularly on one or both sides of the knee. The orthopaedic implant knee hinge may include two elongated plates, each of said elongated plates may have more than one affixation opening therein to accommodate affixation means passing through said affixation opening; said two elongated plates may be pivotally connected to one another at an end thereof by a pivotal connector. The hinge device may further include at least four affixation means to affix the knee hinge to the bones of the femur and tibia, at least two of said at least four affixation means passing through said more than one affixation opening in each of said elongated plates. The openings may be threaded, said affixation means may be a screw and said screw may have a threaded head which cooperates with said threading in said affixation openings.

The affixation means may be a screw and said screw may have threading on the shaft only on the end thereof that will be inserted into the bone. One or both of said elongated plates may include an offset plate to provide for proper placement of said elongated plate along the femur or tibia. The affixation means may be a threaded rod combined with nuts to anchor said elongated plates to said rods. The elongated plates, said attachment means and said pivotal connector may be formed from a material selected from the group consisting of titanium, stainless steel or a bio-compatible polymer material.

The method for minimally invasive insertion of an orthopaedic implant knee hinge may comprising the step providing the orthopaedic implant knee hinge and tunneling said orthopaedic implant knee hinge subcutaneously in the subcutaneous fat layer parallel to the length dimension of the femur and tibia along either the lateral of medial side of the leg. The method may further include the step of attaching the ends of the orthopaedic implant knee hinge to the distal end of the femur and the proximal end of the tibia; said pivotal connector should be located adjacent the distal end of the femur close to the knee joint. The orthopaedic implant knee hinge may remain disposed in the subcutaneous fat layer and away from, but parallel to the femur and tibia once attached thereto.

The surgical method may include the step of tunneling by creating one or more incisions in the skin through which said orthopaedic implant knee hinge can be inserted. The one or more incisions in the skin may be created on the lateral or medial side of the leg near both the distal end of the femur and the proximal end of the tibia. The one or more incisions in the skin may also be created on both the lateral and medial side of the leg near both the distal end of the femur and the proximal end of the tibia, and two orthopaedic implant knee hinges may be implanted, one on the lateral side and one on medial side of the knee.

The step of attaching the ends of the orthopaedic implant knee hinge to the distal end of the femur and the proximal end of the tibia may include inserting at least four affixation means to affix the knee hinge to the bones of the femur and tibia, at least two of said at least four affixation means passing through said more than one affixation opening in each of said elongated plates and into the bone.

DETAILED DESCRIPTION OF THE INVENTION

Figure 2:
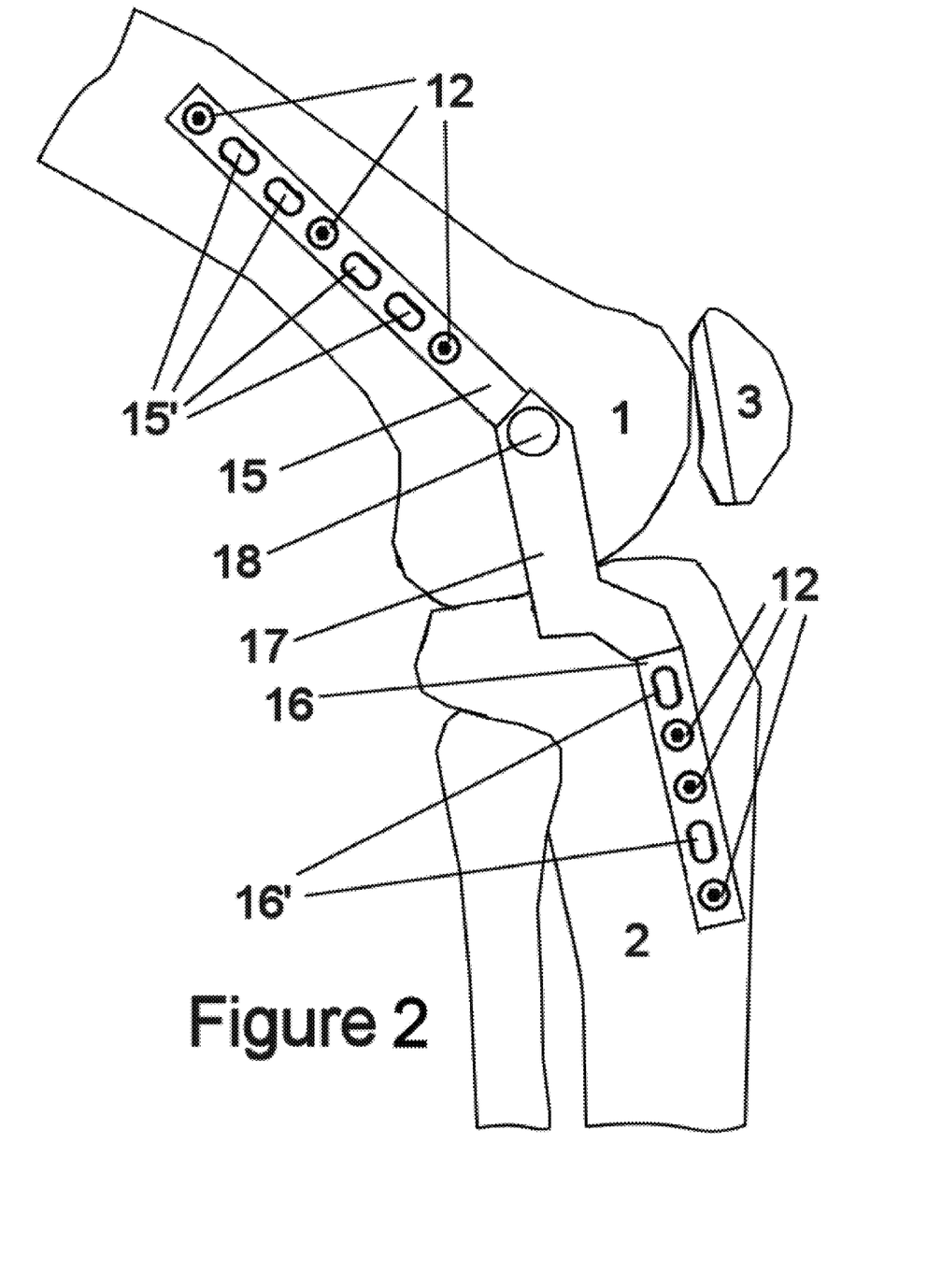
FIG. 2 is a depiction of a side view of a knee joint with the knee hinge of the present invention attached thereto.

The present invention is a knee hinge fixation device and method for application thereof. FIG. 2 is a depiction of a side view of a knee joint with the knee hinge of the present invention attached thereto. The knee joint does not show and of the muscles, ligaments or tendons. In its most basic form the knee hinge is composed of two elongated plates with multiple affixation openings therein.

In FIG. 2, the two elongated plates 15 and 16 are attached to the femur 1 and the tibia 2, respectively. The two elongated plates 15 and 16 are connected together pivotally by a connector 18. The two elongated plates 15 and 16 are connected to the tibia and femur using attachment means 12 which pass through the elongated plates 15 and 16 via affixation openings 15' and 16' and into the femur 1 and tibia 2. As the knee is flexed and extended, the two elongated plates act as a hinge by pivoting at connector 18.

If needed, one or both of the elongated plates may have an offset plate 17 attached thereto to provide for proper placement on the femur and tibia. It should be noted that when the knee hinge is in place, the point of joining between the two elongated plates 15 and 16 at the pivotal connector 18 should be located at the distal end of the femur, to allow for proper extension and flexion of the knee.

Figure 3:
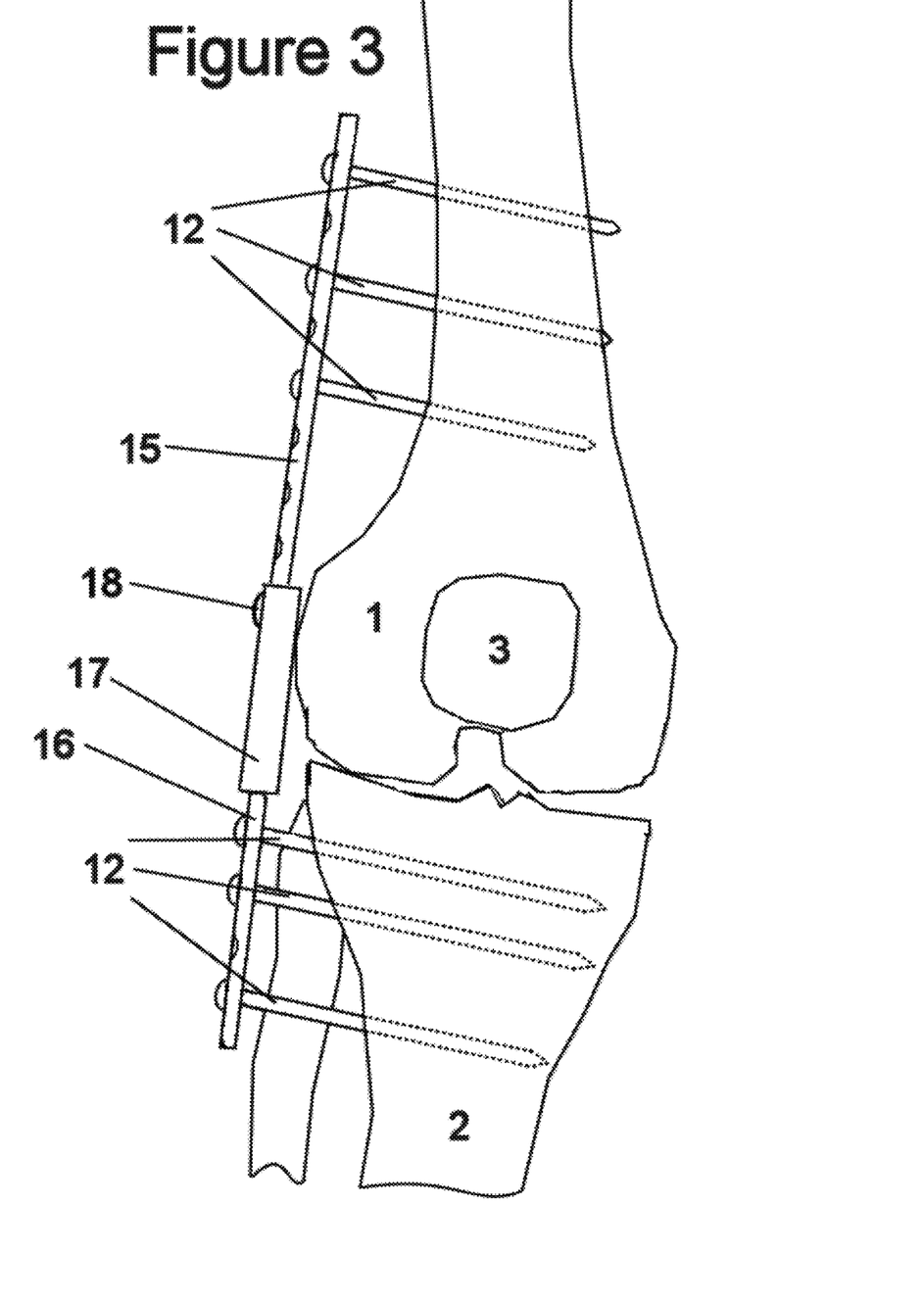
FIG. 3 is a depiction of the front view of the knee joint with the knee hinge of the present invention attached thereto.

FIG. 3 is a depiction of the front view of the knee joint with the knee hinge of the present invention attached thereto. Again the knee joint does not show any of the muscles, ligaments or tendons. FIG. 3 indicates how the elongated plates 15 and 16 are attached to the femur 1 and tibia 2, respectively. It can be seen that the attachments means 12 pass-through the elongated plates via the add fixation openings 15' and 16', and into the bones. It should be noted that the elongated plates of the knee hinge of the present invention are placed subcutaneously but supra-muscularly. This allows for proper stabilization of the knee without having to cut through the muscles and tendons to place the plates against the bones.

Figure 4:
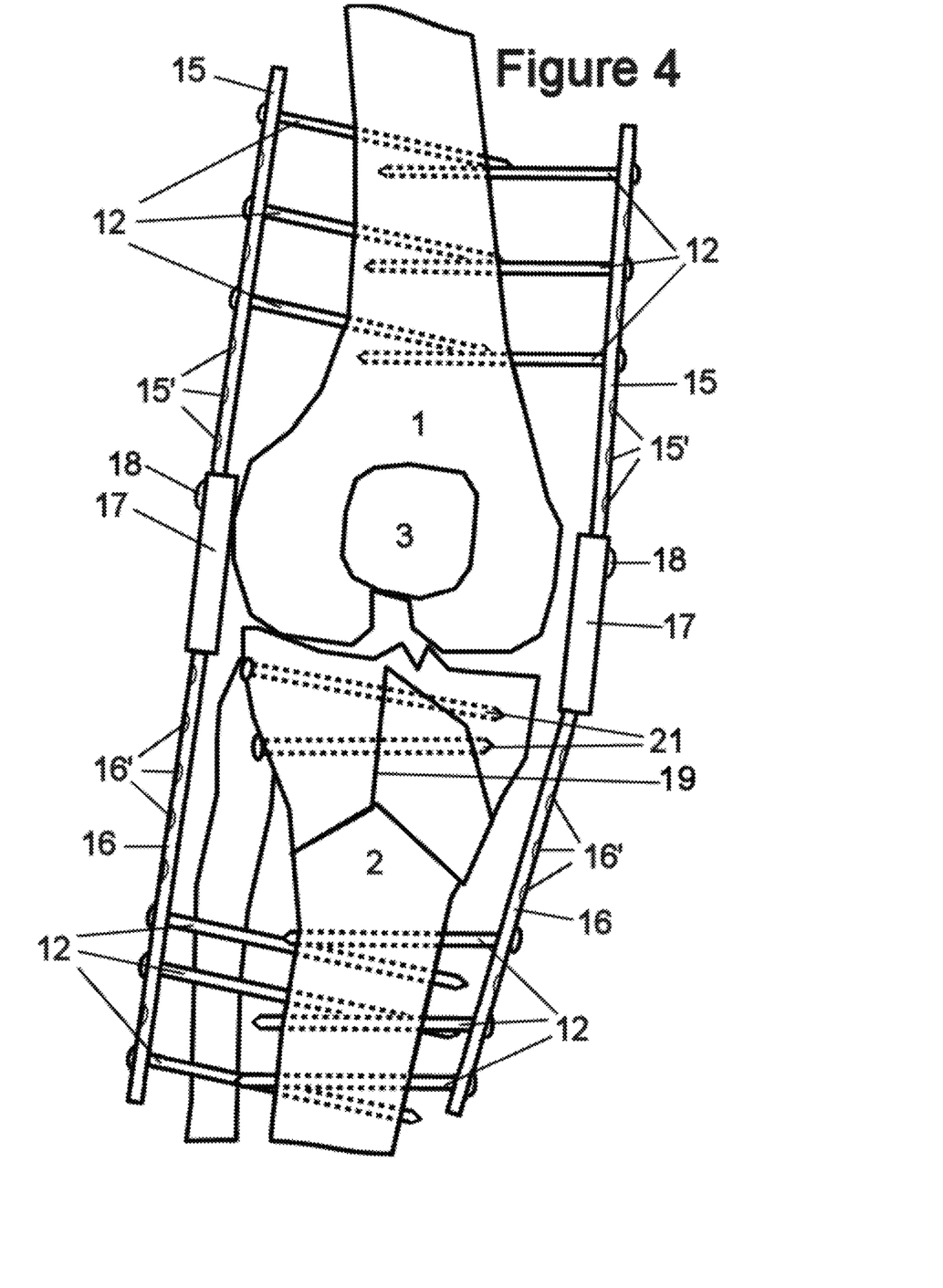
FIG. 4 is a depiction of the front view of the knee joint with two of the knee hinges of the present invention attached thereto along with conventional bone screw fixation of tibial plateau fractures and/or proximal tibia fractures.

FIG. 4 is a depiction of the front view of the knee joint with two of the knee hinges of the present invention attached thereto. Again the knee joint does not show any of the muscles, ligaments or tendons. The knee has tibial plateau fractures 19 and/or proximal tibia fractures 19 which have been conventionally fixed as shown in FIG. 1d using bone screws 21 (the fixation could also have used a bone plate 20 as in FIG. 1e). However, unlike the conventional fixation technique, two of the inventive knee hinges have been inserted subcutaneously (and supra-muscularly) on both the medial and lateral sides of the knee joint. The hinges allow the leg to bear weight and allows for bending of the knee (if appropriate). This allows the patient to retain range of motion in the knee joint from the beginning of the healing process. The hinges also allow the weight of the body to be offloaded from the fracture after fixation and the patient will be able walk on the extremity.

Figure 5:
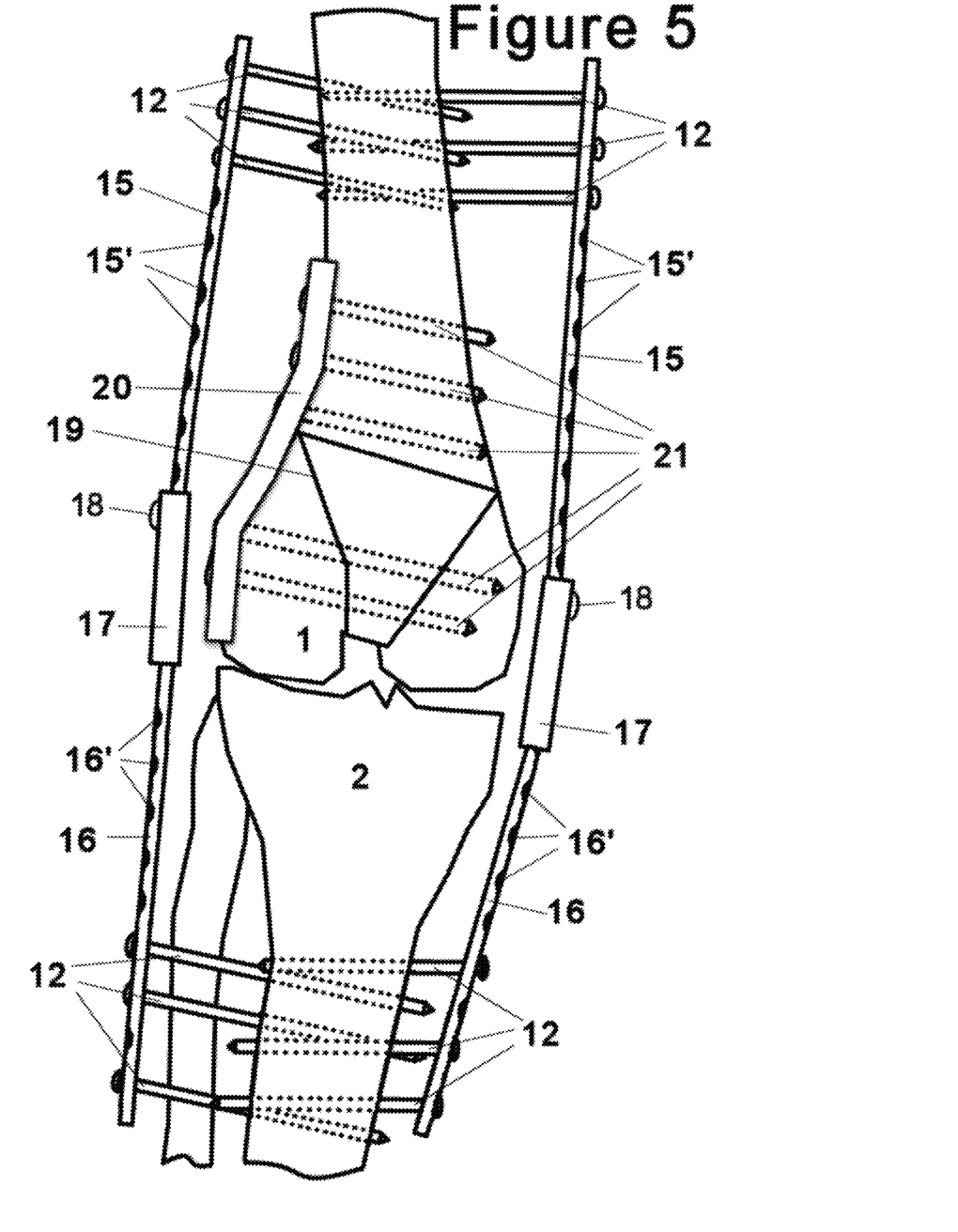
FIG. 5 is a depiction of the front view of the knee joint with two of the knee hinges of the present invention attached thereto along with conventional bone screw and bone plate fixation of supracondylar and intracondylar fractures of the femur.

FIG. 5 is a depiction of the front view of the knee joint with two of the knee hinges of the present invention attached thereto. As before, the knee joint does not show any of the muscles, ligaments or tendons. The knee has supracondylar and intracondylar fractures 19 of the femur which have been conventionally fixed as shown in FIG. 1c using bone screws 21 and a bone plate 20 (the fixation could also have used just bone screws 21 as in FIG. 1b). Again, unlike the conventional fixation technique, two of the inventive knee hinges have been inserted subcutaneously (and supra-muscularly) on both the medial and lateral sides of the knee joint. The hinges allow the leg to bear weight and allow for bending of the knee (if appropriate).

Figure 6:
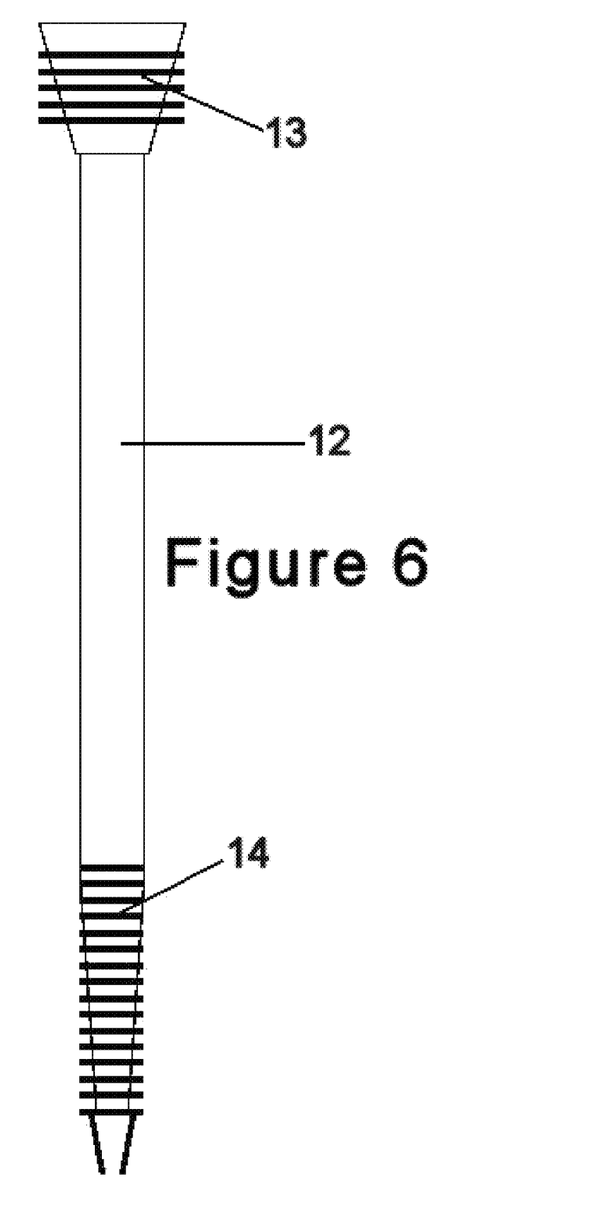
FIG. 6 depicts a preferred affixation means, a screw, useful to affix the inventive knee hinge.

FIG. 6 depicts a preferred affixation means 12, a screw. The screw 12 may preferably have a threaded head 13 which may cooperate with threading in the affixation openings 15' and 16' of the elongated plates 15 and 16. The affixation openings 15' and 16' may be threaded as in locking plate technology. This feature allows the elongated plates 15 and 16 to remain in place subcutaneously but supra-muscularly without being pressed against the muscles, yet holding the bones firmly in place. The screw 12 also preferably has thread 14 only on the end thereof that will be inserted into the bone. Alternatively, a threaded rod may also be used to attach the plates to the bones using nuts or the like to anchor the plates to the rods in the subcutaneous position. The elongated plates 15 and 16, the attachment means 12 and the pivotal connector 18 may be formed from titanium, stainless steel or a bio-compatible polymer material.

The knee hinge may be placed into the subcutaneous fat layer through two incisions in the skin. One incision is near the distal end of the femur 1 and the other is near the proximal end of the tibia 2. The incisions may be approximately two inches or less on each end. Of course, the plates 15 and 16 may come in many different sizes to accommodate different sized people and bones. This placement of the elongated plates 15 and 16 just under the skin prevents disruption of the muscle tissue and since there is no dissection, there is little chance for infection. The hinges may have a locking feature if there is a need to prevent the knee from bending. It should be noted that the hinges are not a permanent implant, but rather should be removed after the injury to knee joint has healed.

It is to be expected that considerable variations may be made in the embodiments disclosed herein without departing from the spirit and scope of this invention. Accordingly, the significant improvements offered by this invention are to be limited only by the scope of the following claims.

I claim:

1. A surgical method for minimally invasive insertion of a subcutaneous orthopaedic implant knee hinge adjacent to a knee joint, said knee joint comprising a femur having a distal end and a tibia having a proximal end, said femur and said tibia having a length dimension, said knee joint having a lateral and a medial side, said method comprising the steps of:

providing an orthopaedic implant knee hinge comprising two elongated plates, each of said elongated plates having more than one affixation opening therein to accommodate subcutaneous affixation means passing through said more than one affixation opening; said two elongated plates being pivotally connected to one another at an end thereof by a pivotal connector, said pivotal connector allowing for only rotational motion of said elongated plates relative to each other at said pivotal connector, another end of each of said two elongated plates being a loose end;

tunneling said orthopaedic implant knee hinge subcutaneously in a subcutaneous fat layer parallel to said length dimension of said femur and said tibia along either said lateral or said medial side of said knee joint; and attaching said loose ends of said orthopaedic implant knee hinge to said distal end of said femur and said proximal end of said tibia; said pivotal connector being located adjacent said distal end of said femur close to said knee joint;

wherein said orthopaedic implant knee hinge remains disposed in said subcutaneous fat layer and away from, but parallel to said femur and said tibia once attached thereto.

2. The surgical method of claim 1, wherein said tunneling step includes creating one or more incisions in the skin through which said orthopaedic implant knee hinge can be inserted.

3. The surgical method of claim 2, wherein said one or more incisions in the skin are created on at least one of said lateral or said medial side of said knee joint near both of said distal end of said femur and said proximal end of said tibia.

4. The surgical method of claim 3, wherein said one or more incisions in the skin are created on both of said lateral side and said medial side of said knee joint near both of said distal end of said femur and said proximal end of said tibia, and a second orthopaedic implant knee hinge is implanted on an opposite side of said knee joint.

5. The surgical method of claim 1, wherein said step of attaching said loose ends of said orthopaedic implant knee hinge to said distal end of said femur and said proximal end of said tibia includes inserting at least four subcutaneous affixation means to affix the knee hinge to said femur and said tibia, at least two of said at least four subcutaneous affixation means passing through said more than one affixation opening in each of said elongated plates and into said femur and said tibia.

6. The surgical method of claim 5, wherein said affixation openings are threaded, said subcutaneous affixation means are screws and said screws have a threaded head which cooperates with said threading in said affixation openings.

7. The surgical method of claim 5, wherein said affixation means are screws and said screws have a shaft and an end thereof that will be inserted into said femur or said tibia of said knee joint, wherein said screws have threading on said shaft only on said end thereof that will be inserted into said femur or said tibia of said knee joint.

8. The surgical method of claim 1, wherein one or both of said elongated plates includes an offset plate to provide for proper placement of said elongated plates along said femur or said tibia.

9. The surgical method of claim 1, wherein said subcutaneous affixation means are threaded rods combined with nuts to anchor said elongated plates to said rods.

10. The surgical method of claim 1, wherein said elongated plates, said subcutaneous attachment means and said pivotal connector are formed from a material selected from the group consisting of titanium, stainless steel or a bio-compatible polymer material.

* * * * *